• US007651493B2

United States Patent
Arts et al.

(10) Patent No.: US 7,651,493 B2
(45) Date of Patent: Jan. 26, 2010

(54) SYSTEM AND METHOD FOR CONTROLLING ELECTROSURGICAL SNARES

(75) Inventors: Gene H. Arts, Berthoud, CO (US);
Jason L. Craig, Loveland, CO (US);
Dale F. Schmaltz, Fort Collins, CO (US)

(73) Assignee: Covidien AG, Neuhausen Am Rheinfall (CH)

( * ) Notice: Subject to any disclaimer, the term of this patent is extended or adjusted under 35 U.S.C. 154(b) by 596 days.

(21) Appl. No.: 11/367,723

(22) Filed: Mar. 3, 2006

(65) Prior Publication Data

US 2007/0208339 A1   Sep. 6, 2007

(51) Int. Cl.
*A61B 18/14* (2006.01)
(52) U.S. Cl. .......................................... 606/47; 606/41
(58) Field of Classification Search ............. 606/32–52
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Dagelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |
| 3,436,563 A | 4/1969 | Regitz |
| 3,439,253 A | 4/1969 | Piteo |

(Continued)

FOREIGN PATENT DOCUMENTS

DE   179607   3/1905

(Continued)

OTHER PUBLICATIONS

International Search Report EP 06010499.9 dated Jan. 29, 2008.

(Continued)

*Primary Examiner*—Michael Peffley
*Assistant Examiner*—Ronald J Hupczey, Jr.

(57) ABSTRACT

A system and method for controlling electrosurgical snares are disclosed. The system includes an electrosurgical instrument having an elongate tubular sheath having proximal and distal ends, the sheath having a longitudinal axis defined therethrough and a shaft having proximal and distal ends. The shaft extends through and is axially movable relative to the sheath. A snare loop is provided at the distal end of the shaft and is configured for encircling tissue. Movement of the shaft relative to the tubular sheath changes the diameter of the exposed snare loop. A feedback sensor operatively connected to the elongated tubular sheath which determines at least one condition of the snare loop, and an electrosurgical generator provides electrosurgical energy to the electrosurgical snare instrument. The generator is configured to receive feedback measurements from the electrosurgical snare instrument and to adjust electrosurgical energy as a function of the measurements.

18 Claims, 6 Drawing Sheets

U.S. PATENT DOCUMENTS

| | | |
|---|---|---|
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,586,120 A | 4/1986 | Malik et al. |
| 4,590,934 A | 5/1986 | Malis et al. |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,911 A | 5/1989 | Broadwin et al. |

| | | | | | |
|---|---|---|---|---|---|
| 4,827,927 A | 5/1989 | Newton | 5,370,675 A | 12/1994 | Edwards et al. |
| 4,832,024 A | 5/1989 | Boussignac et al. | 5,372,596 A | 12/1994 | Klicek et al. |
| 4,848,335 A | 7/1989 | Manes | 5,383,874 A | 1/1995 | Jackson |
| 4,848,355 A | 7/1989 | Nakamura et al. | 5,383,876 A | 1/1995 | Nardella |
| 4,860,745 A | 8/1989 | Farin et al. | 5,383,917 A | 1/1995 | Desai et al. |
| 4,862,889 A | 9/1989 | Feucht | 5,385,148 A | 1/1995 | Lesh et al. |
| 4,880,719 A | 11/1989 | Murofushi et al. | 5,396,062 A | 3/1995 | Eisentraut et al. |
| 4,887,199 A | 12/1989 | Whittle | 5,400,267 A | 3/1995 | Denen et al. |
| 4,890,610 A | 1/1990 | Kirwan et al. | 5,403,311 A | 4/1995 | Abele et al. |
| 4,903,696 A | 2/1990 | Stasz et al. | 5,403,312 A | 4/1995 | Yates et al. |
| 4,907,589 A | 3/1990 | Cosman | 5,409,000 A | 4/1995 | Imran |
| 4,922,210 A | 5/1990 | Flachenecker et al. | 5,409,006 A | 4/1995 | Buchholtz et al. |
| 4,931,047 A | 6/1990 | Broadwin et al. | 5,409,485 A | 4/1995 | Suda |
| 4,931,717 A | 6/1990 | Gray et al. | 5,413,573 A | 5/1995 | Koivukangas |
| 4,938,761 A | 7/1990 | Ensslin | 5,414,238 A | 5/1995 | Steigerwald et al. |
| 4,942,313 A | 7/1990 | Kinzel | 5,417,719 A | 5/1995 | Hull et al. |
| 4,959,606 A | 9/1990 | Forge | 5,422,567 A | 6/1995 | Matsunaga |
| 4,961,047 A | 10/1990 | Carder | 5,423,808 A | 6/1995 | Edwards et al. |
| 4,961,435 A | 10/1990 | Kitagawa et al. | 5,423,809 A | 6/1995 | Klicek |
| 4,966,597 A | 10/1990 | Cosman | 5,423,810 A | 6/1995 | Goble et al. |
| RE33,420 E | 11/1990 | Sussman | 5,425,704 A | 6/1995 | Sakurai et al. |
| 4,969,885 A | 11/1990 | Farin | 5,430,434 A | 7/1995 | Lederer et al. |
| 4,992,719 A | 2/1991 | Harvey | 5,432,459 A | 7/1995 | Thompson |
| 4,993,430 A | 2/1991 | Shimoyama et al. | 5,433,739 A | 7/1995 | Sluijter et al. |
| 4,995,877 A | 2/1991 | Ams et al. | 5,434,398 A | 7/1995 | Goldberg |
| 5,015,227 A | 5/1991 | Broadwin et al. | 5,436,566 A | 7/1995 | Thompson |
| 5,019,176 A | 5/1991 | Brandhorst, Jr. | 5,438,302 A | 8/1995 | Goble |
| 5,024,668 A | 6/1991 | Peters et al. | 5,443,463 A | 8/1995 | Stern et al. |
| 5,026,371 A | 6/1991 | Rydell et al. | 5,445,635 A | 8/1995 | Denen |
| 5,029,588 A | 7/1991 | Yock et al. | 5,451,224 A | 9/1995 | Goble et al. |
| 5,087,257 A | 2/1992 | Farin | 5,458,597 A | 10/1995 | Edwards et al. |
| 5,099,840 A | 3/1992 | Goble et al. | 5,462,521 A | 10/1995 | Brucker et al. |
| 5,103,804 A | 4/1992 | Abele et al. | 5,472,441 A | 12/1995 | Edwards et al. |
| 5,108,389 A | 4/1992 | Cosmescu | 5,472,443 A | 12/1995 | Cordis et al. |
| 5,108,391 A | 4/1992 | Flachenecker | 5,478,303 A | 12/1995 | Foley-Nolan et al. |
| 5,122,137 A | 6/1992 | Lennox | 5,480,399 A | 1/1996 | Hebborn |
| 5,133,711 A | 7/1992 | Hagen | 5,483,952 A | 1/1996 | Aranyi |
| 5,151,102 A | 9/1992 | Kamiyama et al. | 5,490,850 A | 2/1996 | Ellman et al. |
| 5,152,762 A | 10/1992 | McElhenney | 5,496,312 A | 3/1996 | Klicek |
| 5,157,603 A | 10/1992 | Scheller et al. | 5,496,313 A | 3/1996 | Gentelia et al. |
| 5,158,561 A | 10/1992 | Rydell et al. | 5,500,012 A | 3/1996 | Brucker et al. |
| 5,160,334 A | 11/1992 | Billings et al. | 5,500,616 A | 3/1996 | Ochi |
| 5,162,217 A | 11/1992 | Hartman | 5,514,129 A | 5/1996 | Smith |
| 5,167,658 A | 12/1992 | Ensslin | 5,520,684 A | 5/1996 | Imran |
| 5,190,517 A | 3/1993 | Zieve et al. | 5,531,774 A | 7/1996 | Schulman et al. |
| 5,190,542 A | 3/1993 | Nakao et al. | 5,534,018 A | 7/1996 | Wahlstrand et al. |
| 5,196,008 A | 3/1993 | Kuenecke | 5,536,267 A | 7/1996 | Edwards et al. |
| 5,196,009 A | 3/1993 | Kirwan, Jr. | 5,540,681 A | 7/1996 | Strul et al. |
| 5,201,900 A | 4/1993 | Nardella | 5,540,683 A | 7/1996 | Ichikawa |
| 5,207,691 A | 5/1993 | Nardella | 5,540,684 A | 7/1996 | Hassler, Jr. |
| 5,230,623 A | 7/1993 | Guthrie et al. | 5,540,724 A | 7/1996 | Cox |
| 5,233,515 A | 8/1993 | Cosman | 5,556,396 A | 9/1996 | Cohen et al. |
| 5,249,121 A | 9/1993 | Baum et al. | 5,558,671 A | 9/1996 | Yates |
| 5,254,117 A | 10/1993 | Rigby et al. | 5,569,242 A | 10/1996 | Lax et al. |
| RE34,432 E | 11/1993 | Bertrand | 5,571,147 A | 11/1996 | Sluijter et al. |
| 5,267,994 A | 12/1993 | Gentelia et al. | 5,573,533 A | 11/1996 | Strul |
| 5,267,997 A | 12/1993 | Farin | 5,584,830 A | 12/1996 | Ladd et al. |
| 5,281,213 A | 1/1994 | Milder et al. | 5,588,432 A | 12/1996 | Crowley |
| 5,300,068 A | 4/1994 | Rosar et al. | 5,594,636 A | 1/1997 | Schauder |
| 5,300,070 A | 4/1994 | Gentelia | 5,596,466 A | 1/1997 | Ochi |
| 5,318,563 A | 6/1994 | Malis et al. | 5,599,344 A | 2/1997 | Paterson |
| 5,323,778 A | 6/1994 | Kandarpa et al. | 5,599,345 A | 2/1997 | Edwards et al. |
| 5,324,283 A | 6/1994 | Heckele | 5,599,348 A | 2/1997 | Gentelia et al. |
| 5,330,518 A | 7/1994 | Neilson et al. | 5,605,150 A | 2/1997 | Radons et al. |
| 5,334,183 A | 8/1994 | Wuchinich | 5,613,966 A | 3/1997 | Makower et al. |
| 5,334,193 A | 8/1994 | Nardella | 5,613,996 A | 3/1997 | Lindsay |
| 5,341,807 A | 8/1994 | Nardella | 5,625,370 A | 4/1997 | D'Hont |
| 5,342,356 A | 8/1994 | Ellman | 5,626,575 A | 5/1997 | Crenner |
| 5,342,357 A | 8/1994 | Nardella | 5,628,745 A | 5/1997 | Bek |
| 5,342,409 A | 8/1994 | Mullett | 5,643,330 A | 7/1997 | Holsheimer et al. |
| 5,348,554 A | 9/1994 | Imran et al. | 5,647,869 A | 7/1997 | Goble et al. |
| 5,370,645 A | 12/1994 | Klicek et al. | 5,647,871 A | 7/1997 | Levine et al. |
| 5,370,672 A | 12/1994 | Fowler et al. | 5,651,780 A | 7/1997 | Jackson et al. |

| | | | | | | |
|---|---|---|---|---|---|---|
| 5,658,322 A | 8/1997 | Fleming | | 6,063,078 A | 5/2000 | Wittkampf |
| 5,660,567 A | 8/1997 | Nierlich et al. | | 6,068,627 A | 5/2000 | Orszulak et al. |
| 5,674,217 A | 10/1997 | Wahlstrom et al. | | 6,074,386 A | 6/2000 | Goble et al. |
| 5,685,840 A | 11/1997 | Schechter et al. | | 6,074,388 A | 6/2000 | Tockweiler et al. |
| 5,688,267 A | 11/1997 | Panescu et al. | | 6,080,149 A | 6/2000 | Huang et al. |
| 5,690,692 A | 11/1997 | Fleming | | 6,093,186 A | 7/2000 | Goble |
| 5,693,042 A | 12/1997 | Boiarski et al. | | 6,102,497 A | 8/2000 | Ehr et al. |
| 5,694,304 A | 12/1997 | Telefus et al. | | RE36,871 E | 9/2000 | Epstein |
| 5,695,494 A | 12/1997 | Becker | | 6,113,591 A | 9/2000 | Whayne et al. |
| 5,696,351 A | 12/1997 | Benn et al. | | 6,113,596 A | 9/2000 | Hooven |
| 5,696,441 A | 12/1997 | Mak et al. | | 6,123,702 A | 9/2000 | Swanson et al. |
| 5,702,386 A | 12/1997 | Stern et al. | | 6,132,429 A | 10/2000 | Baker |
| 5,702,429 A | 12/1997 | King | | 6,142,992 A | 11/2000 | Cheng et al. |
| 5,707,369 A | 1/1998 | Vaitekunas et al. | | 6,155,975 A | 12/2000 | Urich et al. |
| 5,712,772 A | 1/1998 | Telefus et al. | | 6,162,217 A | 12/2000 | Kannenberg et al. |
| 5,713,896 A | 2/1998 | Nardella | | 6,171,304 B1 | 1/2001 | Netherly et al. |
| 5,718,246 A | 2/1998 | Vona | | 6,188,211 B1 | 2/2001 | Rincon-Mora et al. |
| 5,720,744 A | 2/1998 | Eggleston et al. | | 6,203,541 B1 | 3/2001 | Keppel |
| 5,722,975 A | 3/1998 | Edwards et al. | | 6,210,403 B1 | 4/2001 | Klicek |
| 5,729,448 A | 3/1998 | Haynie et al. | | 6,222,356 B1 | 4/2001 | Taghizadeh-Kaschani |
| 5,733,281 A | 3/1998 | Nardella | | 6,228,080 B1 | 5/2001 | Gines |
| 5,738,683 A * | 4/1998 | Osypka ................. 606/47 | | 6,228,081 B1 | 5/2001 | Goble |
| 5,749,869 A | 5/1998 | Lindenmeier et al. | | 6,231,569 B1 | 5/2001 | Bek |
| 5,749,871 A | 5/1998 | Hood et al. | | 6,235,020 B1 | 5/2001 | Cheng et al. |
| 5,755,715 A | 5/1998 | Stern | | 6,238,387 B1 | 5/2001 | Miller, III |
| 5,766,165 A | 6/1998 | Gentelia et al. | | 6,238,388 B1 | 5/2001 | Ellman |
| 5,769,847 A | 6/1998 | Panescu | | 6,241,725 B1 | 6/2001 | Cosman |
| 5,772,659 A | 6/1998 | Becker et al. | | 6,245,065 B1 | 6/2001 | Panescu |
| 5,792,138 A | 8/1998 | Shipp | | 6,246,912 B1 | 6/2001 | Sluijter et al. |
| 5,797,802 A | 8/1998 | Nowak | | 6,251,106 B1 | 6/2001 | Becker et al. |
| 5,797,902 A | 8/1998 | Netherly | | 6,258,085 B1 | 7/2001 | Eggleston |
| 5,814,092 A | 9/1998 | King | | 6,261,285 B1 | 7/2001 | Novak |
| 5,817,093 A | 10/1998 | Williamson, IV et al. | | 6,261,286 B1 | 7/2001 | Goble et al. |
| 5,820,568 A | 10/1998 | Willis | | 6,273,886 B1 | 8/2001 | Edwards |
| 5,827,271 A | 10/1998 | Bussey et al. | | 6,275,786 B1 | 8/2001 | Daners |
| 5,830,212 A | 11/1998 | Cartmell | | 6,293,941 B1 | 9/2001 | Strul |
| 5,836,909 A | 11/1998 | Cosmescu | | 6,293,942 B1 | 9/2001 | Goble et al. |
| 5,836,943 A | 11/1998 | Miller, III | | 6,296,636 B1 | 10/2001 | Cheng et al. |
| 5,836,990 A | 11/1998 | Li | | 6,306,131 B1 | 10/2001 | Hareyama et al. |
| 5,846,236 A | 12/1998 | Lindenmeier et al. | | 6,306,134 B1 | 10/2001 | Goble et al. |
| 5,868,737 A | 2/1999 | Taylor et al. | | 6,309,386 B1 | 10/2001 | Bek |
| 5,868,739 A | 2/1999 | Lindenmeier et al. | | 6,325,799 B1 | 12/2001 | Goble |
| 5,868,740 A | 2/1999 | LeVeen et al. | | 6,337,998 B1 | 1/2002 | Behl et al. |
| 5,871,481 A | 2/1999 | Kannenberg et al. | | 6,338,657 B1 | 1/2002 | Harper et al. |
| 5,897,552 A | 4/1999 | Edwards et al. | | 6,350,262 B1 | 2/2002 | Ashley |
| 5,906,620 A | 5/1999 | Nakao et al. | | 6,358,245 B1 | 3/2002 | Edwards |
| 5,908,444 A | 6/1999 | Azure | | 6,364,877 B1 | 4/2002 | Goble et al. |
| 5,913,882 A | 6/1999 | King | | 6,371,963 B1 * | 4/2002 | Nishtala et al. ............. 606/113 |
| 5,921,982 A | 7/1999 | Lesh et al. | | 6,383,183 B1 | 5/2002 | Sekino et al. |
| 5,925,070 A | 7/1999 | King et al. | | 6,391,024 B1 | 5/2002 | Sun et al. |
| 5,931,836 A | 8/1999 | Hatta et al. | | 6,398,779 B1 | 6/2002 | Buysse et al. |
| 5,938,690 A | 8/1999 | Law et al. | | 6,398,781 B1 | 6/2002 | Goble et al. |
| 5,948,007 A | 9/1999 | Starkebaum et al. | | 6,402,741 B1 | 6/2002 | Keppel et al. |
| 5,951,545 A | 9/1999 | Schilling | | 6,402,743 B1 | 6/2002 | Orszulak et al. |
| 5,951,546 A | 9/1999 | Lorentzen | | 6,416,509 B1 | 7/2002 | Goble et al. |
| 5,954,686 A | 9/1999 | Garito et al. | | 6,436,096 B1 | 8/2002 | Hareyama |
| 5,954,717 A | 9/1999 | Behl et al. | | 6,451,015 B1 | 9/2002 | Rittman, III et al. |
| 5,954,719 A | 9/1999 | Chen et al. | | 6,458,121 B1 | 10/2002 | Rosenstock |
| 5,961,344 A | 10/1999 | Rosales et al. | | 6,464,689 B1 | 10/2002 | Qin |
| 5,971,980 A | 10/1999 | Sherman | | 6,464,696 B1 | 10/2002 | Oyama |
| 5,976,128 A | 11/1999 | Schilling et al. | | 6,498,466 B1 | 12/2002 | Edwards |
| 5,983,141 A | 11/1999 | Sluijter et al. | | 6,506,189 B1 | 1/2003 | Rittman, III et al. |
| 6,010,499 A | 1/2000 | Cobb | | 6,508,815 B1 | 1/2003 | Strul |
| 6,014,581 A | 1/2000 | Whayne et al. | | 6,511,476 B2 | 1/2003 | Hareyama |
| 6,015,415 A | 1/2000 | Avellanet | | 6,511,478 B1 | 1/2003 | Burnside et al. |
| 6,033,399 A | 3/2000 | Gines | | 6,517,538 B1 | 2/2003 | Jacob et al. |
| 6,044,283 A | 3/2000 | Fein et al. | | 6,524,308 B1 | 2/2003 | Muller et al. |
| 6,053,910 A | 4/2000 | Fleenor | | 6,547,786 B1 | 4/2003 | Goble |
| 6,053,912 A | 4/2000 | Panescu et al. | | 6,558,376 B2 | 5/2003 | Bishop |
| 6,055,458 A | 4/2000 | Cochran et al. | | 6,560,470 B1 | 5/2003 | Pologe |
| 6,056,745 A | 5/2000 | Panescu et al. | | 6,562,037 B2 | 5/2003 | Paton |
| 6,056,746 A | 5/2000 | Goble et al. | | 6,565,559 B2 | 5/2003 | Eggleston |
| 6,063,075 A | 5/2000 | Mihori | | 6,573,248 B2 | 6/2003 | Ramasamy et al. |

| | | | | | | |
|---|---|---|---|---|---|---|
| 6,575,969 B1 | 6/2003 | Rittman, III et al. | | 7,250,746 B2 | 7/2007 | Oswald et al. |
| 6,582,427 B1 | 6/2003 | Goble et al. | | 7,255,694 B2 | 8/2007 | Keppel |
| 6,620,157 B1 | 9/2003 | Dabney et al. | | 7,282,048 B2 | 10/2007 | Goble et al. |
| 6,623,423 B2 | 9/2003 | Sakurai | | 7,300,435 B2 | 11/2007 | Wham et al. |
| 6,629,973 B1 | 10/2003 | Wardell et al. | | 7,303,557 B2 | 12/2007 | Wham et al. |
| 6,635,057 B2 | 10/2003 | Harano | | 7,364,577 B2 | 4/2008 | Wham et al. |
| 6,645,198 B1 | 11/2003 | Bommannan et al. | | 7,367,972 B2 | 5/2008 | Francischelli et al. |
| 6,648,883 B2 | 11/2003 | Francischelli | | RE40,388 E | 6/2008 | Gines |
| 6,652,514 B2 | 11/2003 | Ellman | | 7,396,336 B2 | 7/2008 | Orszulak et al. |
| 6,663,623 B1 | 12/2003 | Oyama et al. | | 2001/0014804 A1 | 8/2001 | Goble et al. |
| 6,663,624 B2 | 12/2003 | Edwards | | 2001/0029315 A1 | 10/2001 | Sakurai et al. |
| 6,666,860 B1 | 12/2003 | Takahashi | | 2001/0031962 A1 | 10/2001 | Eggleston |
| 6,679,875 B2 | 1/2004 | Honda | | 2002/0035363 A1 | 3/2002 | Edwards et al. |
| 6,682,527 B2 | 1/2004 | Strul | | 2002/0035364 A1 | 3/2002 | Schoenman et al. |
| 6,685,700 B2 | 2/2004 | Behl | | 2002/0052599 A1 | 5/2002 | Goble |
| 6,685,701 B2 | 2/2004 | Orszulak et al. | | 2002/0068932 A1 | 6/2002 | Edwards |
| 6,685,703 B2 | 2/2004 | Pearson et al. | | 2002/0107517 A1 | 8/2002 | Witt et al. |
| 6,689,131 B2 | 2/2004 | McClurken | | 2002/0111624 A1 | 8/2002 | Witt et al. |
| 6,692,489 B1 | 2/2004 | Heim | | 2002/0151889 A1 | 10/2002 | Swanson et al. |
| 6,693,782 B1 | 2/2004 | Lash | | 2002/0193787 A1 | 12/2002 | Qin |
| 6,712,813 B2 | 3/2004 | Ellman | | 2003/0004510 A1 | 1/2003 | Wham et al. |
| 6,730,080 B2 | 5/2004 | Harano | | 2003/0060818 A1 | 3/2003 | Kannenberg |
| 6,733,495 B1 | 5/2004 | Bek | | 2003/0078572 A1 | 4/2003 | Pearson et al. |
| 6,733,498 B2 | 5/2004 | Paton | | 2003/0139741 A1 | 7/2003 | Goble et al. |
| 6,740,079 B1 | 5/2004 | Eggers | | 2003/0153908 A1 | 8/2003 | Goble |
| 6,740,085 B2 | 5/2004 | Hareyama | | 2003/0163123 A1 | 8/2003 | Goble |
| 6,755,825 B2 | 6/2004 | Shoenman et al. | | 2003/0163124 A1 | 8/2003 | Goble |
| 6,758,846 B2 | 7/2004 | Goble et al. | | 2003/0171745 A1 | 9/2003 | Francischelli |
| 6,783,523 B2 | 8/2004 | Qin | | 2003/0181898 A1 | 9/2003 | Bowers |
| 6,786,905 B2 | 9/2004 | Swanson et al. | | 2003/0199863 A1 | 10/2003 | Swanson |
| 6,790,206 B2 | 9/2004 | Panescu | | 2003/0225401 A1 | 12/2003 | Eggers et al. |
| 6,796,981 B2 | 9/2004 | Wham | | 2004/0002745 A1 | 1/2004 | Flemming |
| 6,824,539 B2 | 11/2004 | Novak | | 2004/0015159 A1 | 1/2004 | Slater et al. |
| 6,830,569 B2 | 12/2004 | Thompson | | 2004/0015163 A1 | 1/2004 | Buysse et al. |
| 6,843,789 B2 | 1/2005 | Goble | | 2004/0015216 A1 | 1/2004 | DeSisto |
| 6,849,073 B2 | 2/2005 | Hoey | | 2004/0019347 A1 | 1/2004 | Sakurai |
| 6,855,141 B2 | 2/2005 | Lovewell | | 2004/0024395 A1 | 2/2004 | Ellman |
| 6,855,142 B2 | 2/2005 | Harano | | 2004/0030328 A1 | 2/2004 | Eggers |
| 6,860,881 B2 | 3/2005 | Sturm | | 2004/0030330 A1 | 2/2004 | Brassell et al. |
| 6,864,686 B2 | 3/2005 | Novak | | 2004/0044339 A1 | 3/2004 | Beller |
| 6,875,210 B2 | 4/2005 | Refior | | 2004/0049179 A1 | 3/2004 | Francischelli |
| 6,893,435 B2 | 5/2005 | Goble | | 2004/0054365 A1 | 3/2004 | Goble |
| 6,923,804 B2 | 8/2005 | Eggers et al. | | 2004/0059323 A1 | 3/2004 | Sturm et al. |
| 6,929,641 B2 | 8/2005 | Goble et al. | | 2004/0068304 A1 | 4/2004 | Paton |
| 6,939,346 B2 | 9/2005 | Kannenberg et al. | | 2004/0082946 A1 | 4/2004 | Malis |
| 6,939,347 B2 | 9/2005 | Thompson | | 2004/0095100 A1 | 5/2004 | Thompson |
| 6,942,660 B2 | 9/2005 | Pantera et al. | | 2004/0097912 A1 | 5/2004 | Gonnering |
| 6,948,503 B2 | 9/2005 | Refior et al. | | 2004/0097914 A1 | 5/2004 | Pantera |
| 6,966,907 B2 | 11/2005 | Goble | | 2004/0097915 A1 | 5/2004 | Refior |
| 6,989,010 B2 | 1/2006 | Francischelli et al. | | 2004/0116919 A1 | 6/2004 | Heim |
| 6,994,704 B2 | 2/2006 | Qin et al. | | 2004/0133189 A1 | 7/2004 | Sakurai |
| 6,994,707 B2 | 2/2006 | Ellman et al. | | 2004/0138653 A1 | 7/2004 | Dabney et al. |
| 7,001,381 B2 | 2/2006 | Harano et al. | | 2004/0138654 A1 | 7/2004 | Goble |
| 7,004,174 B2 | 2/2006 | Eggers et al. | | 2004/0143263 A1 | 7/2004 | Schechter et al. |
| 7,041,096 B2 | 5/2006 | Malis et al. | | 2004/0147918 A1 | 7/2004 | Keppel |
| 7,044,948 B2 | 5/2006 | Keppel | | 2004/0167508 A1 | 8/2004 | Wham et al. |
| 7,044,949 B2 | 5/2006 | Orszulak et al. | | 2004/0172016 A1 | 9/2004 | Bek |
| 7,060,063 B2 | 6/2006 | Marion et al. | | 2004/0193148 A1 | 9/2004 | Wham et al. |
| 7,062,331 B2 | 6/2006 | Zarinetchi et al. | | 2004/0230189 A1 | 11/2004 | Keppel |
| 7,063,692 B2 | 6/2006 | Sakurai et al. | | 2004/0243120 A1 | 12/2004 | Orszulak et al. |
| 7,066,933 B2 | 6/2006 | Hagg | | 2004/0260279 A1 | 12/2004 | Goble |
| 7,122,031 B2 | 10/2006 | Edwards et al. | | 2005/0004564 A1 | 1/2005 | Wham |
| 7,131,860 B2 | 11/2006 | Sartor et al. | | 2005/0004569 A1 | 1/2005 | Witt et al. |
| 7,137,980 B2 | 11/2006 | Buysse et al. | | 2005/0021020 A1 | 1/2005 | Blaha et al. |
| 7,147,638 B2 | 12/2006 | Chapman et al. | | 2005/0021022 A1 | 1/2005 | Sturm et al. |
| 7,160,293 B2 | 1/2007 | Sturm et al. | | 2005/0101949 A1 | 5/2005 | Harano et al. |
| 7,172,591 B2 | 2/2007 | Harano et al. | | 2005/0101951 A1 | 5/2005 | Wham |
| 7,175,618 B2 | 2/2007 | Dabney et al. | | 2005/0113818 A1 | 5/2005 | Sartor |
| 7,175,621 B2 | 2/2007 | Heim et al. | | 2005/0113819 A1 | 5/2005 | Wham |
| 7,211,081 B2 | 5/2007 | Goble | | 2005/0113823 A1* | 5/2005 | Reschke et al. .............. 606/42 |
| 7,214,224 B2 | 5/2007 | Goble | | 2005/0149151 A1 | 7/2005 | Orszulak |
| 7,220,260 B2 | 5/2007 | Fleming et al. | | 2005/0182398 A1 | 8/2005 | Paterson |
| 7,247,155 B2 | 7/2007 | Hoey et al. | | 2005/0197659 A1 | 9/2005 | Bahney |

| | | | | | | |
|---|---|---|---|---|---|---|
| 2005/0203504 | A1 | 9/2005 | Wham et al. | EP | 1500378 | 1/2005 |
| 2006/0025760 | A1 | 2/2006 | Podhajsky | EP | 1535581 | 6/2005 |
| 2006/0079871 | A1 | 4/2006 | Plaven et al. | EP | 1609430 | 12/2005 |
| 2006/0161148 | A1 | 7/2006 | Behnke | EP | 1645235 | 4/2006 |
| 2006/0178664 | A1 | 8/2006 | Keppel | EP | 0880220 B1 | 6/2006 |
| 2006/0224152 | A1 | 10/2006 | Behnke et al. | EP | 1707143 | 10/2006 |
| 2006/0281360 | A1 | 12/2006 | Sartor et al. | EP | 1810628 | 7/2007 |
| 2007/0038209 | A1 | 2/2007 | Buysse et al. | EP | 1810630 | 7/2007 |
| 2007/0093800 | A1 | 4/2007 | Wham et al. | EP | 1810633 | 7/2007 |
| 2007/0093801 | A1 | 4/2007 | Behnke | FR | 1275415 | 10/1961 |
| 2007/0135812 | A1 | 6/2007 | Sartor | FR | 1347865 | 11/1963 |
| 2007/0173802 | A1 | 7/2007 | Keppel | FR | 2313708 | 12/1976 |
| 2007/0173803 | A1 | 7/2007 | Wham et al. | FR | 2502935 | 10/1982 |
| 2007/0173804 | A1 | 7/2007 | Wham et al. | FR | 2517953 | 6/1983 |
| 2007/0173805 | A1 | 7/2007 | Weinberg et al. | FR | 2573301 | 5/1986 |
| 2007/0173806 | A1 | 7/2007 | Orszulak et al. | GB | 607850 | 9/1948 |
| 2007/0173810 | A1 | 7/2007 | Orszulak | GB | 855459 | 11/1960 |
| 2007/0173813 | A1 | 7/2007 | Odom | GB | 902775 | 8/1962 |
| 2007/0208339 | A1 | 9/2007 | Arts et al. | GB | 2164473 | 3/1986 |
| 2007/0225698 | A1 | 9/2007 | Orszulak et al. | GB | 2214430 | 9/1989 |
| 2007/0250052 | A1 | 10/2007 | Wham | GB | 2358934 A | 8/2001 |
| 2007/0265612 | A1 | 11/2007 | Behnke et al. | SU | 166452 | 1/1965 |
| 2007/0282320 | A1 | 12/2007 | Buysse et al. | SU | 727201 | 4/1980 |
| 2008/0015564 | A1 | 1/2008 | Wham et al. | WO | WO92/06642 | 4/1992 |
| 2008/0039831 | A1 | 2/2008 | Odom et al. | WO | WO93/24066 | 12/1993 |
| 2008/0039836 | A1 | 2/2008 | Odom et al. | WO | WO94/24949 | 11/1994 |
| 2008/0082094 | A1 | 4/2008 | McPherson et al. | WO | WO94/28809 | 12/1994 |
| 2008/0125767 | A1 | 5/2008 | Blaha | WO | WO95/09577 | 4/1995 |

FOREIGN PATENT DOCUMENTS

| | | | | | |
|---|---|---|---|---|---|
| DE | 1099658 | 2/1961 | WO | WO95/19148 | 7/1995 |
| DE | 1139927 | 11/1962 | WO | WO96/02180 | 2/1996 |
| DE | 1149832 | 6/1963 | WO | WO96/04860 | 2/1996 |
| DE | 1439302 | 1/1969 | WO | WO96/08794 | 3/1996 |
| DE | 2439587 | 2/1975 | WO | WO96/18349 | 6/1996 |
| DE | 2455174 | 5/1975 | WO | WO96/29946 | 10/1996 |
| DE | 2407559 | 8/1975 | WO | WO96/39086 | 12/1996 |
| DE | 2602517 | 7/1976 | WO | WO96/39914 | 12/1996 |
| DE | 2504280 | 8/1976 | WO | WO97/06739 | 2/1997 |
| DE | 2540968 | 3/1977 | WO | WO97/06740 | 2/1997 |
| DE | 2820908 | 11/1978 | WO | WO97/06855 | 2/1997 |
| DE | 2803275 | 8/1979 | WO | WO97/11648 | 4/1997 |
| DE | 2823291 | 11/1979 | WO | WO97/17029 | 5/1997 |
| DE | 2946728 | 5/1981 | WO | WO02/11634 | 2/2002 |
| DE | 3143421 | 5/1982 | WO | WO02/45589 | 6/2002 |
| DE | 3045996 | 7/1982 | WO | WO02/47565 | 6/2002 |
| DE | 3120102 | 12/1982 | WO | WO02/053048 | 7/2002 |
| DE | 3510586 | 10/1986 | WO | WO02/088128 | 7/2002 |
| DE | 3604823 | 8/1987 | WO | WO03/090630 | 11/2003 |
| DE | 390937 | 4/1989 | WO | WO03/090635 | 11/2003 |
| DE | 3905558 | 8/1990 | WO | WO03/092520 | 11/2003 |
| DE | 3942998 | 7/1991 | WO | WO2005/060365 | 11/2003 |
| DE | 4339049 A1 | 5/1995 | WO | WO2004/028385 | 4/2004 |
| DE | 19717411 | 11/1998 | WO | WO2004/098385 | 4/2004 |
| DE | 19848540 A1 | 5/2000 | WO | WO2004/103156 | 12/2004 |
| EP | 246350 | 11/1987 | WO | WO2005/046496 | 5/2005 |
| EP | 310431 | 4/1989 | WO | WO2005/048809 | 6/2005 |
| EP | 325456 | 7/1989 | WO | WO2005/050151 | 6/2005 |
| EP | 336742 | 10/1989 | WO | WO2005048809 A1 | 6/2005 |
| EP | 390937 | 10/1990 | WO | WO2005/060849 | 7/2005 |
| EP | 556705 | 8/1993 | | | |
| EP | 0569130 A1 | 11/1993 | | | |
| EP | 608609 | 8/1994 | | | |
| EP | 0694291 | 1/1996 | | | |
| EP | 836868 | 4/1998 | | | |
| EP | 878169 | 11/1998 | | | |
| EP | 1051948 | 11/2000 | | | |
| EP | 1053720 | 11/2000 | | | |
| EP | 1151725 | 11/2001 | | | |
| EP | 1293171 | 3/2003 | | | |
| EP | 1472984 | 11/2004 | | | |
| EP | 1495712 | 1/2005 | | | |

OTHER PUBLICATIONS

International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.

Muller et al., "Extended Left Hemicolectomy Using the LigaSure Vessel Sealing System" Innovations That Work; Sep. 1999.
International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2; (Mar. 2005); 160-164.
International Search Report EP 07008207.8; dated Sep. 5, 2007.
International Search Report EP 07010673.7; dated Sep. 24, 2007.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., A Numerical Study of Rapid Heating for High Temperature Radio Frequency Hyperthermia International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al. "Studies on Coagulation and the Development of an Automatic Computerized Bipolar Coagulator" J.Neurosurg, vol. 75, Jul. 1991, pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman at al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedance" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1p. Sep. 1998.
Ogden Goertzel Alternative to the Fourier Transform: Jun. 1993 pp. 485-487 Electronic World; Reed Business Publishing, Sutton, Surrey, BG vol. 99, No. 9, 1687.
Sugita et al., "Bipolar Coagulator with Automatic Thermocontrol" J. Neurisurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.

* cited by examiner

SYSTEM AND METHOD FOR CONTROLLING ELECTROSURGICAL SNARES

BACKGROUND

1. Technical Field

The present disclosure relates generally to an electrosurgical snare instrument and, more particularly, to a system and method for controlling energy delivered by an electrosurgical generator to the electrosurgical snare instrument based on diameter and pressure of the snare.

2. Background of Related Art

Snare instruments are electrosurgical devices that are primarily used for removing small growths from the lining of internal body cavities (e.g., polyps within the bowels), such as during polypectomy procedures. These snares include a wire loop configured to encircle the small growth, and then electrosurgical energy is applied to the tissue to cut and/or coagulate. Generally, snare instruments include an elongate tubular member having a handle, such as a sheath, a shaft extending through the tubular member having a wire loop connected to the distal end ("distal" refers to that portion that is further from the user, while "proximal" refers to that portion that is closer to the user or surgeon) thereof. The loop is opened by pushing the shaft toward the distal end thereby moving/extracting the loop outside the tubular member and is closed by pulling the shaft toward the proximal end thereby moving/retracting the loop inside the tubular member.

The snare instrument is generally inserted into internal body cavities through an endoscope. In the case of a polypectomy, the instrument is inserted through the gastrointestinal tract and moved toward the polyp(s) marked for removal. During insertion, the loop is retracted into the shaft, and once at the removal site, it is extracted and is expanded around the polyp. The surgeon then constricts the loop around the polyp and electrosurgical energy is applied thereto.

Currently, snare instruments are used without providing any sensory feedback to the generator. The surgeon has to manually adjust the energy delivered to the snare while simultaneously adjusting the pressure exacted on the polyp by the loop. For instance, as the surgeon increases the pressure, the energy must also increase so that the energy increases proportionally with pressure. The contiguous increase in pressure and energy allows for the polyp to be removed only after the stalk portion thereof has been cauterized. Increasing energy too slowly may detrimentally affect removal of the polyp causing bleeding. Increasing energy too rapidly may result in damage to the surrounding tissue. Presently, the success of these surgical procedures depended on the experience of the surgeon to control the pressure and energy delivered to the snare instrument. Such manual control of these operating factors is not infallible.

SUMMARY

The present disclosure provides for a system and method of controlling delivery of electrosurgical energy supplied by a generator to an electrosurgical snare instrument based on the position and pressure of the snare loop. The snare instrument is configured for removal of polyps and includes a position sensor configured to determine diameter of the snare loop and a pressure sensor configured to determine the pressure exacted on the polyp. The position and pressure feedback signals are transmitted to the generator, which then automatically adjusts the power of output, mode, and other factors affecting electrosurgical energy.

According to one embodiment of the present disclosure, an electrosurgical snare instrument is disclosed. The instrument includes an elongate tubular sheath having proximal and distal ends, the sheath having a longitudinal axis defined therethrough. The instrument also includes a shaft having proximal and distal ends, the shaft extending through and axially movable relative to the sheath. A snare loop is provided at the distal end of the shaft and is configured for encircling tissue. Movement of the shaft relative to the tubular sheath changes the diameter of the exposed snare loop. A feedback sensor operatively connected to the elongated tubular sheath determines at least one condition of the snare loop.

According to another embodiment of the present disclosure, a system for controlling an electrosurgical snare instrument is disclosed. The system includes an electrosurgical instrument having an elongate tubular sheath having proximal and distal ends, the sheath having a longitudinal axis defined therethrough and a shaft having proximal and distal ends. The shaft extends through and is axially movable relative to the sheath. A snare loop is provided at the distal end of the shaft and is configured for encircling tissue. Movement of the shaft relative to the tubular sheath changes the diameter of the exposed snare loop. A feedback sensor operatively connected to the elongated tubular sheath determines at least one condition of the snare loop, and an electrosurgical generator provides electrosurgical energy to the electrosurgical snare instrument. The generator is configured to receive feedback measurements from the electrosurgical snare instrument and to adjust electrosurgical energy as a function of the measurements.

According to a further embodiment of the present disclosure, a method for controlling an electrosurgical snare instrument is disclosed. The method includes the step of inserting an electrosurgical snare instrument into a body cavity. The instrument includes an elongate tubular sheath having proximal and distal ends, the sheath having a longitudinal axis defined therethrough. The instrument also includes a shaft having proximal and distal ends, the shaft extending through and axially movable relative to the sheath. A snare loop is provided at the distal end of the shaft and is configured for encircling tissue. Movement of the shaft relative to the tubular sheath changes the diameter of the exposed snare loop. The method further includes the steps of positioning the snare loop to encircle a portion of the tissue and collecting feedback measurements through a feedback sensor operatively connected to the elongated tubular sheath for determining at least one condition of the snare loop indicative of at least one condition of the snare loop. The method further includes the steps of transmitting feedback measurements to an electrosurgical generator, which provides electrosurgical current and adjusting electrosurgical energy as a function of the feedback measurements.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure are described below with reference to the accompanying drawings. In the following description, well-known functions or constructions are not described in detail to avoid obscuring the present disclosure in unnecessary detail. As used herein, the term "distal" refers to that portion that is further from the user while the term "proximal" refers to that portion that is closer to the user or surgeon.

Figure 1:
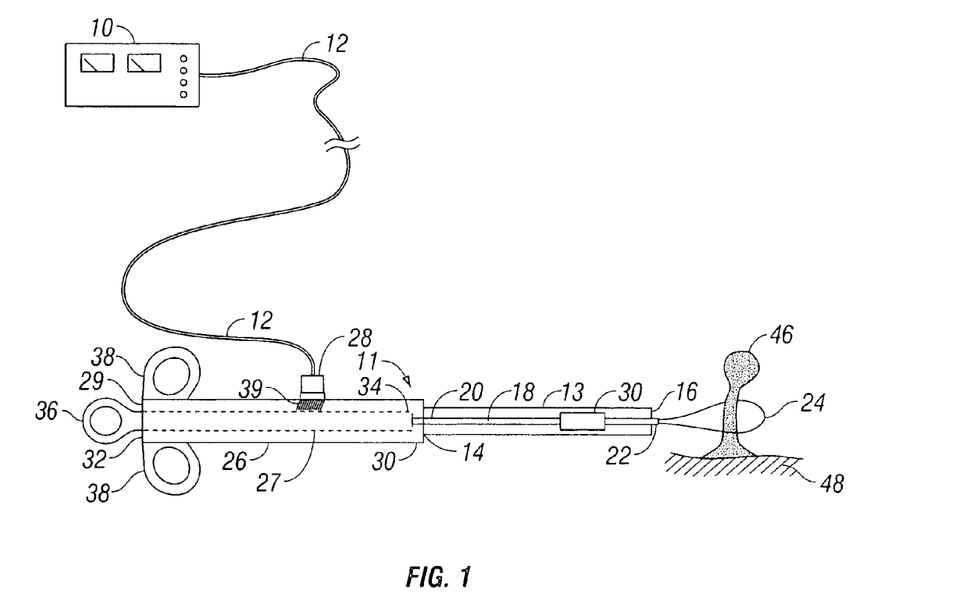
FIG. 1 is a diagram illustrating an electrosurgical system including a snare instrument according to the present disclosure.

FIG. 1 shows an electrosurgical system including a generator 10 that supplies electrosurgical energy to an electrosurgical snare instrument 11 through electrical wiring within a cable 12. The generator 10 also includes processing means (e.g., one or more microprocessors, storage, memory, etc.) configured to analyze control and input signals as discussed in more detail below. The snare instrument 11 includes an elongate tubular sheath 13 having a proximal end 14 and a distal end 16 formed preferably from a suitable medical grade plastic, such as Teflon, polyurethane, polyethylene and the like. The sheath 13 has an outside diameter sufficiently small enough to allow the sheath 13 to fit through a working lumen of an endoscope (not explicitly shown).

The snare instrument 11 also includes an electrically conductive shaft 18 having a proximal end 20 and a distal end 22 extending through and axially movable within the sheath 12. The shaft 18 may be in a form a multifilament twisted and drawn or swaged cable where the filaments are metallic, such as stainless steel, a nickel-titanium alloy, and the like. It is envisioned that the shaft 18 may be formed from a suitable plastic material, such as the plastic used to form the sheath 13, wherein the plastic includes an electrically conductive surface (e.g., coating, foil, etc.).

Figure 2:
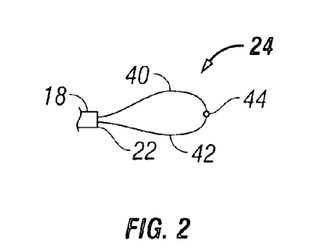
FIG. 2 is a schematic diagram illustrating a snare loop.

A snare loop 24 is mechanically and electrically coupled to the distal end 22 of shaft 18 via a connector 30 near distal end 16 of the sheath 12 as illustrated in FIG. 2. The snare loop 24 is formed from suitable wire, such as multifilament wire used to form the shaft 18. In the illustrated embodiment, the snare loop 24 includes two sides 40, 42 with corresponding two ends attached to the distal end 22 of the shaft 18 to form a loop by welding, soldering, or crimping. Alternatively, the shaft 18 may be formed from two cables or wires twined together from the proximal end 20 and the distal end 22 and untwined after the distal end to form the loop 24. In an alternative embodiment, the two sides 40, 42 may be formed from separate wire or cable elements coupled together at the distal end 22 of the shaft 18 and the distal end 44.

The snare instrument 11 further includes a handle assembly 26 having a distal end 30 and a proximal end 29. The sheath 13 is connected to the assembly 26 at the distal end 30. The assembly 26 may have tubular structure and may be formed by molding from an inflexible plastic material or formed by other processes from other inflexible medical grade materials (e.g., stainless steel). The assembly 26 may also be formed from elastic medical grade materials (e.g., high durometer urethane).

Within the assembly 26 is a plunger 27 having a distal end 34 and a proximal end 32. The plunger 27 is electrically conductive and inflexible. The plunger 27 may be formed entirely from metal (e.g., steel rod) or from an inflexible plastic having an electrically conductive surface. The shaft 18 is connected to the plunger 27 at the shaft's proximal end 20 and plunger's distal end 34. The plunger 27 includes a first handle 36 at the proximal end 32 thereof, which allows the surgeon in conjunction with a second handle 38 disposed at the proximal end 29 of the assembly 26 to manipulate the shaft 18 and the loop 24 by moving the shaft 18 along the longitudinal axis. The second handle 38 includes finger rests adapted to receive the forefinger and index finger of the surgeon whereby the thumb is inserted into the first handle 36 to facilitate the manipulation of the plunger 27 and the shaft 18.

Disposed on the surface of the assembly 26 is a cautery connector 28 that is conductively coupled via a brush connector 39 to the shaft 18 through the plunger 27 so that the plunger 27 and the shaft 18 can be and moved longitudinally while maintaining such conductive coupling.

The snare instrument 11 can be adapted for monopolar and bipolar electrosurgical procedures. In monopolar configuration, the loop 24 serves as an active electrode through which electrosurgical energy will be applied to the tissue. In such a configuration, a return electrode (not shown) will be attached to a patient to return the current supplied through the loop 24 to the generator 10.

In bipolar configuration, the active and return electrodes are incorporated into the loop 24. One of the two sides 40, 42 serves as an active electrode while the other serves as a return electrode being separated by an insulative material (e.g., ceramic tip) at the distal end 44.

Referring back to FIG. 1, the loop 24 is shown surrounding a stalk of a polyp 46 extending outward from the surface of a hollow organ 48 in the gastrointestinal tract (e.g., bowel). During an operating procedure, the snare instrument 11 is inserted into the organ through an endoscope channel and the endoscope is used to visually locate and assess the shape and type of the polyp 46 as is well known in the art. Thereafter, the surgeon positions the snare instrument 11 within the organ and places the loop 24 around the polyp 46. Then, the surgeon retracts the loop 24 by pulling the plunger 27 toward the proximal end 32 to close the loop 24 around the polyp 46. Once the loop 24 is closed and in contact around polyp 46, the surgeon applies the coagulation current to desiccate the cells of the polyp 46, thereby severing the growth. After the severing, the surgeon switches the generator 10 into coagulating mode and places the closed loop 24 in contact with severed blood vessels of the polyp 46 to close the vessels and stop the blood flow. It is known that the loop 24 in a closed configuration may also be used to remove polyps too small to be encircled by the loop 24. Those skilled in the art will appreciate that the surgeon may also use coagulating current initially to coagulate the blood vessels within the polyp 46 and then use the cutting current to cut across or proximate the coagulated portion.

Figure 3:
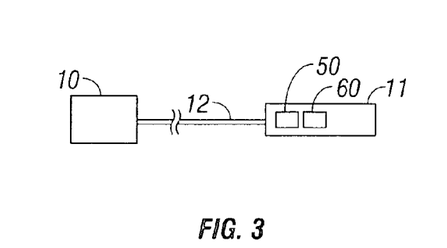
FIG. 3 is a block diagram of the electrosurgical system of FIG. 1.

To aid the surgeon in adjustment of various parameters (e.g., intensity, waveform, etc.) of the electrosurgical energy, the present disclosure provides a position sensor 50 and a pressure sensor 60 disposed within the snare instrument 11, as shown in FIG. 3, which provide feedback to the generator 10 upon which the generator 10 makes adjustment to operating parameters, such as power output, power versus impedance curves, operating mode, duty cycle, etc. The pressure sensor 60 senses the pressure exerted by the loop 24 on the polyp 46. The position sensor 50 senses the diameter of the loop 24 (i.e., perimeter and/or size of the loop 24) and reports the measurements to the generator 10, which then makes a determination based on the measurements and makes corresponding adjustments to electrosurgical energy.

More particularly, when the loop 24 is not fully closed but in contact with the polyp 46 the position sensor 50 and the pressure sensor 60 report that fact to the generator 10, which then communicates electrosurgical energy through the loop 24 so that the polyp 46 can be severed. When the loop 24 is fully closed, e.g., the polyp 46 has been fully severed, that information is forwarded by the sensors 50, 60 to the generator 10, which then switches into coagulation mode to coagulate the blood vessels. Those skilled in the art will appreciate that the generator 10 may be programmed to respond in different ways than those discussed above (e.g., coagulate when loop 24 is in contact with tissue and cut when the loop 24 is closed). The snare instrument 11 may include either one of, or both, the position sensor 50 and the pressure sensor 60 allowing the generator 10 to make power and other adjustments based on diameter and/or pressure measurements.

Figure 4:
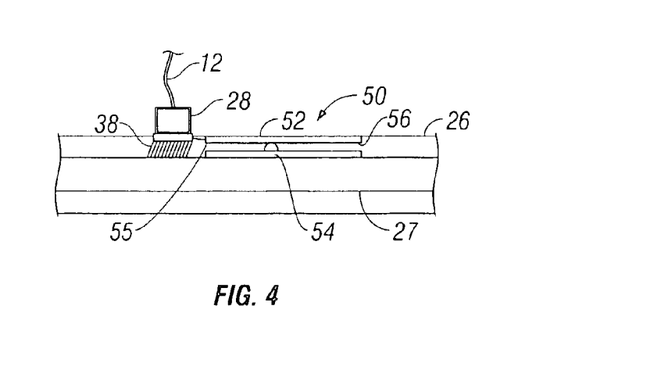
FIG. 4 is a cross sectional view of the snare instrument including a position sensor.
Figure 4A:
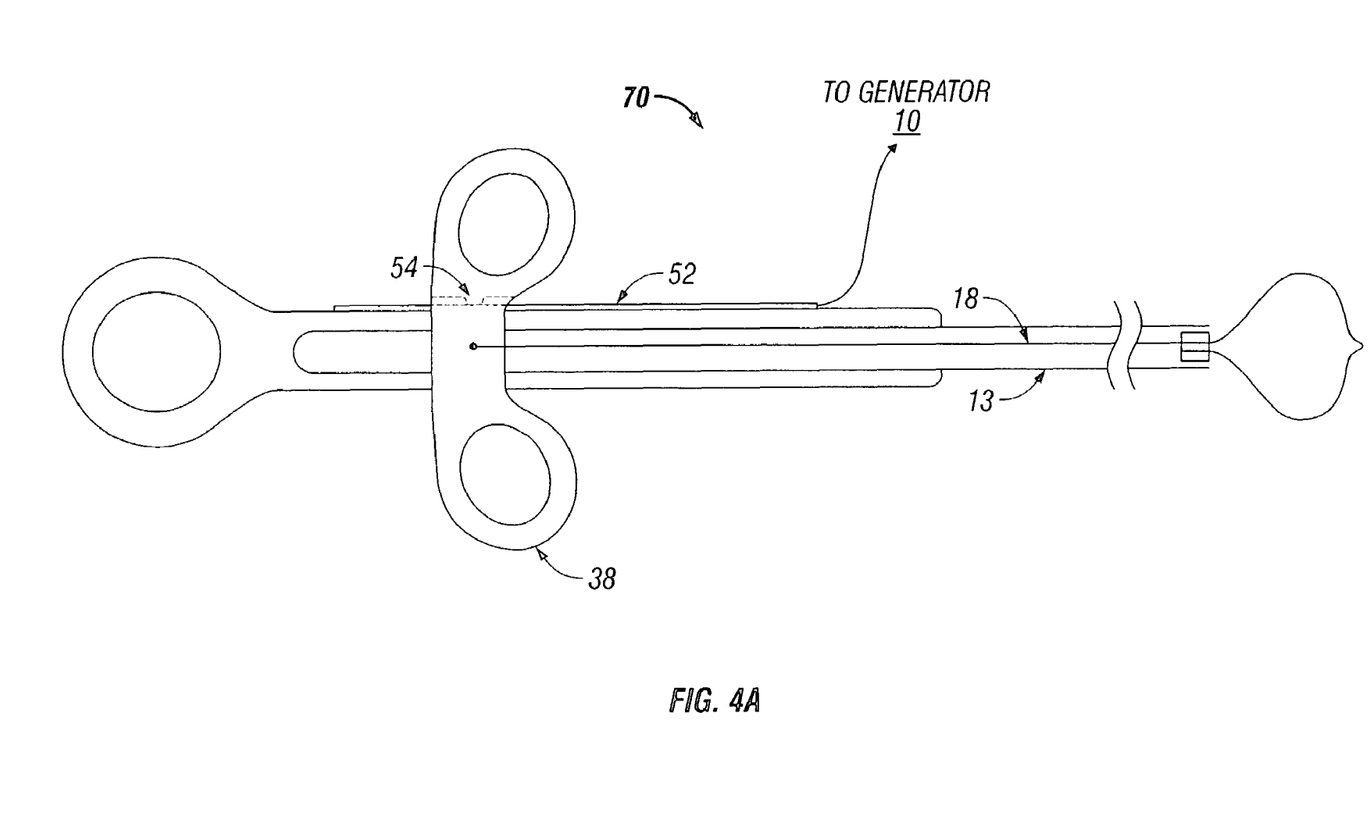
FIG. 4A is a cross sectional view of an alternate snare instrument.

With reference to FIG. 4, the position sensor 50 is shown disposed within the assembly 26. In one embodiment, the position sensor 50 includes a film-type potentiometer 52 coupled to the inner surface of the tubular structure of the assembly 26 and a contact nub 54 in contact therewith. The nub 54 is positioned on the outer surface of the plunger 27 directly opposite the potentiometer 52. The potentiometer 52 and the nub 54 may be relocated (e.g., their positions reversed) as long as these components of the position sensor 50 are kept in contact with and are positioned opposite each other. Furthermore, the potentiometer 52 may be disposed on the inner surface of the sheath 13 with the nub 54 being located on the shaft 18. The nub 54 may also be disposed (e.g., embedded) within the second handle 38 and the potentiometer 52 may be placed on the outer surface of sheath 13, as shown in FIG. 4A.

The spring sensor 60 may be constructed in the following manner. The sheath 13 and other components of the snare instrument 70 may be made from elastic materials and thereby be used to spring-load the loop 24. The spring-loading produces a signal from the position sensor 50 embedded in the second handle 38 and measures both the snare size of the loop 24 and the pressure exerted thereby.

Figure 4B:
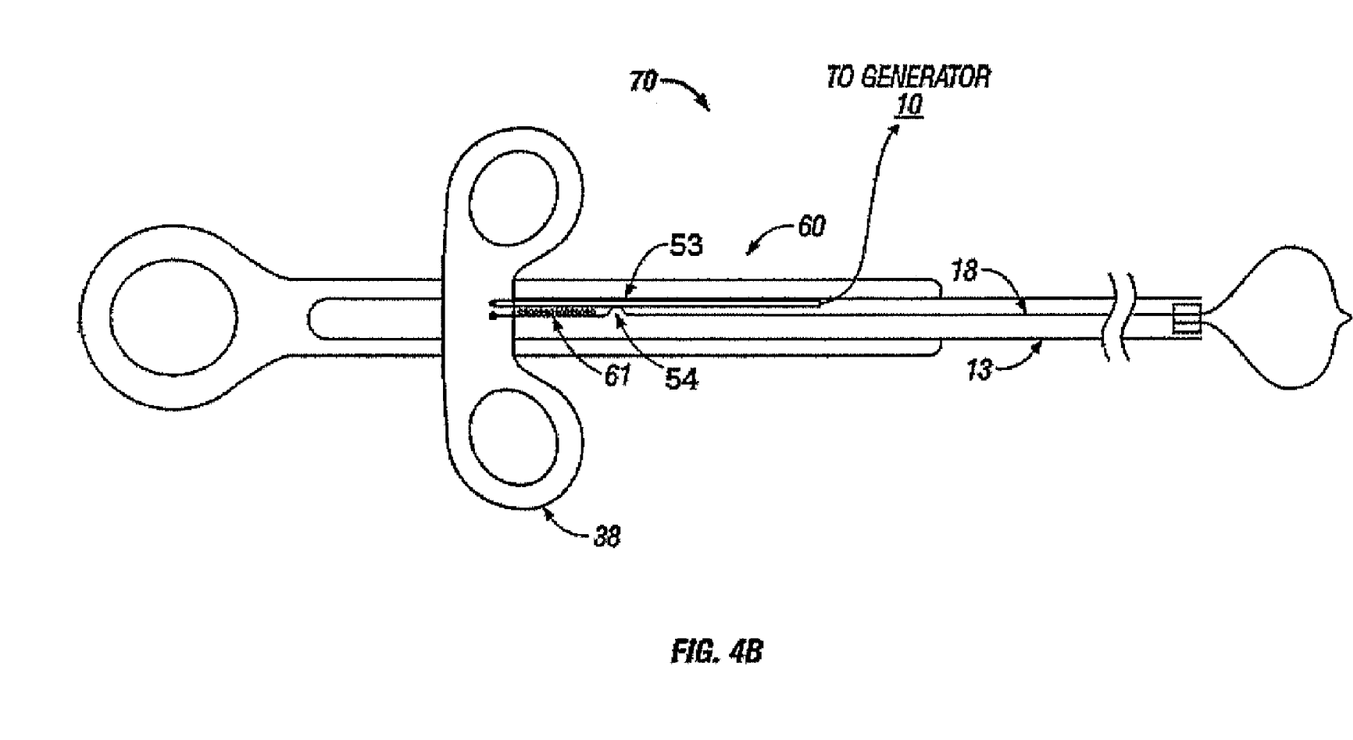
FIG. 4B is a cross sectional view of an alternate snare instrument.

With reference to FIG. 4B, a pressure sensor 60 is shown that includes the nub 54 disposed within the sheath 13 and in contact with a second potentiometer 53. The nub 54 is coupled to the second handle 38 through a suitable elastic member 61 (e.g., a spring) connected in series thereto. The position of the nub 54 and its contact with the potentiometer 53 is directly proportional to the force with which the second handle 38 is pushed pack (e.g., counterbalanced by the elastic member 61). Therefore, the pressure exerted by loop 24 may be determined by measuring the signal generated by the nub 54 contacting the potentiometer 53. The pressure sensor 60 may also be a piezoelectric crystal. The piezoelectric crystal converts pressure applied thereto into corresponding voltage that can then be converted into a digital signal and be processed by the processing means of the generator 10.

Figure 4C:
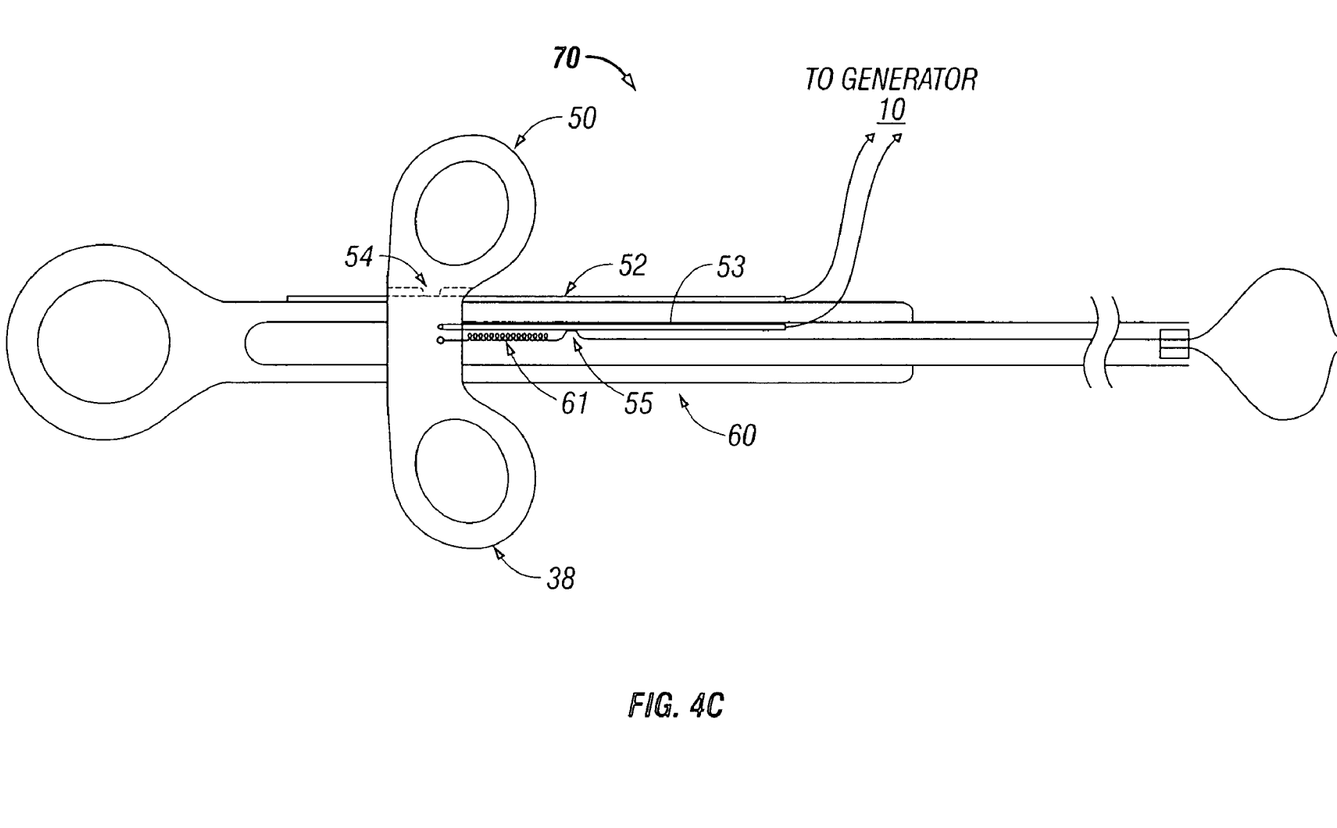
FIG. 4C is a cross sectional view of an alternate snare instrument.

As shown in FIG. 4C, the pressure and position sensors 50, 60 are disposed within the snare instrument 70. The position sensor 50 measures the diameter of the loop 24 using the position of the nub 54 and the pressure sensor 60 measures the pressure exerted by the loop 24 by determining the position of the nub 54 as affected by the elastic member 61.

The feedback concerning the diameter of the loop 24 is reported to the generator 10 through control wires disposed within the cable 12. As the plunger 27 is moved longitudinally within the handle assembly 26, the nub 54 slides longitudinally across the surface of the potentiometer 52. When the nub 54 is in contact with the potentiometer 52 near a proximal end 55 thereof, a corresponding voltage is transmitted to the generator 10. The voltage is analyzed by the generator 10 to determine the control signal, which when the nub 54 is near or at the proximal end 55, denotes that the loop 24 is in closed position (e.g., shaft 18 is fully retracted). When nub 54 is in contact with the potentiometer 52 near a distal end 56, the voltage transmitted to the generator 10 signals that the loop 24 is fully opened. Positions of the nub 54 in between the proximal and distal ends 55, 56 can be configured to denote other corresponding control signals (e.g., partially closed loop 24). After analyzing the control signals and determining the position of the loop 24, the generator 10 makes appropriate changes to the output of the electrosurgical energy, such as output power, waveform, voltage, impedance, mode, etc.

In addition to providing feedback on the position and diameter of the loop 24, the present disclosure also provides for a system and method to determine the pressure exerted by the loop 24 on the polyp 46 using the pressure sensor 60, as shown in FIG. 3. Determining the snare loop 24 pressure may be important in determining when power must be applied to the polyp 46. As discussed above, initially power is applied to the polyp, more specifically, a coagulation mode is used. Conventionally, surgeons had to figure out when to sever the polyp based on experience. The pressure sensor 60 allows for automatic adjustment by providing feedback to the generator 10 concerning the pressure applied to the polyp 46. When the pressure sensor 60 senses that the pressure is at its highest, it denotes that the loop 24 is firmly fitted around the polyp 46. This information is transmitted to the generator 10 which increases power or switches operational modes (e.g., cutting mode) and supplies electrosurgical energy to the snare instrument 11. As soon as the polyp 46 is severed, the pressure applied by the loop 24 dissipates since the physical obstruction (e.g., polyp 46) has been removed. This change in pressure is also transmitted to the generator 10 which then modifies the operating mode and supplies coagulating current to the snare instrument 11 to coagulate the blood vessels.

The pressure sensor 60 may enable the surgeon to regulate the pressure such that the surgeon can effectively seal the blood vessels prior to resection of the polyp 46. For example, the surgeon may be able to control the pressure applied around the polyp 46 to within an ideal parameter known to effectively seal tissue rather than simply coagulate tissue. Other features may also have to be properly controlled to create an effective seal, such as gap distance between opposing surfaces of the loop 24 and energy control.

Where elastic compliance of the materials comprising the components of the snare instrument 70 are known, a single position sensor may be used to sense position as well as the pressure of the snare. In particular, the position measurement signal in conjunction with the elastic properties may be used to calculate the pressure and position of the snare based on a single signal. Conventional materials used in construction of snare instruments are prone to compress and stretch when force is applied to the handle. Therefore, placing the position sensor 50 at the handle 38 allows for measuring the position and the pressure of the snare. A single pressure sensor 60 may be used to determine both the position and the pressure of the snare from the pressure signal based on the elastic compliance of the flexible snare materials.

The snare instrument 70 may include an impedance sensor (not explicitly shown) that measures impedance of the tissue at the polyp 46. Using a sensing current the impedance sensor determines when sufficient energy has been communicated to the polyp 46 to signal the polyp 46 has been coagulated and may be severed. Impedance measurements may also be used to determine when other stages of the procedure have been accomplished, since as energy is applied to the polyp 46 impedance of the tissue changes, which allows for measurements and/or determinations regarding the state of the polyp 46.

Those skilled in the art will appreciate that the generator 10 includes a specific operating mode designed for snare procedures. Snare procedures differ from other electrosurgical operations (e.g., sealing blood vessels, cutting tissue, etc.) because the electrode in snare procedures (e.g., loop 24) is in continuous tissue contact. As a result snare procedures are characterized by low impedance of the tissue and low voltage requirements. The generator 10 of the present disclosure includes a new operating mode that changes output power, waveform, and voltage relative to the tissue impedance. This operating mode may be also useful in other electrosurgical procedures having same characteristics as snare procedures where an active electrode is in continuous tissue contact.

Figure 5:
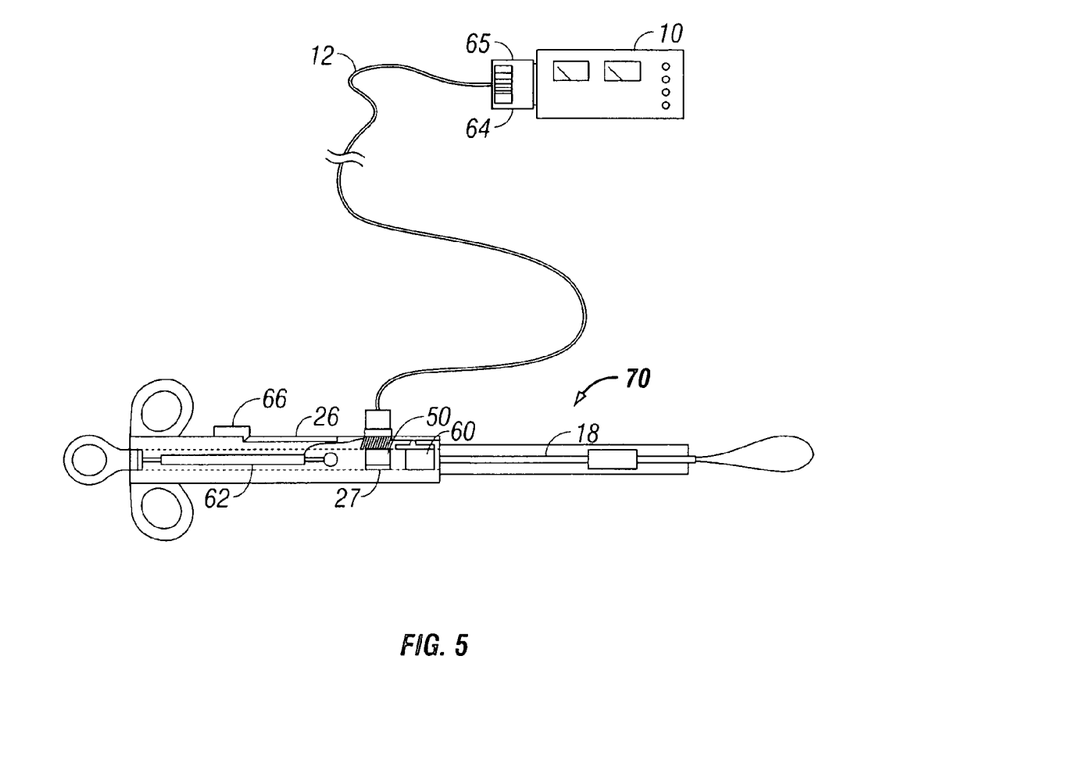
FIG. 5 is a diagram illustrating an alternate embodiment of an electrosurgical system according to the present disclosure.

Pressure and loop diameter feedback can also be used to fully automate snare procedures by using a snare instrument 70 as shown in FIG. 5. The application of electrosurgical energy as well as diameter control of the loop 24 may be controlled by the generator 10 based on the feedback received from the sensors 50, 60. The snare instrument 70 includes an actuator 62, such as a piston cylinder which is electrically controlled by the generator 10 or a cable controller actuated by a pulley system. An algorithm for controlling the actuator 62 is programmed in the generator 10 and may be activated by scanning a barcode 64 attached to a plug 65. It is well known in the art to identify devices by scanning barcodes and loading preprogrammed algorithms into the electrosurgical generators based on that information. The generator 10 may include a reader for scanning barcodes and other identifying means.

The snare instrument 70 also includes a button 66 that activates the snare instrument 70 once it is in position (e.g., the loop 24 is placed around the polyp 46). Once the proper positioning is achieved, the surgeon presses the button 66 to activate the generator 10 algorithm. The generator 10 adjusts the diameter of the loop 24 by decreasing the diameter gradually. More particularly, the generator 10 signals the actuator 62 to contract, thereby pulling the shaft 18 and contracting the loop 24. The contraction continues until the pressure sensor 60 reports to the generator 10 that the loop 24 is in tight contact with the polyp 46. The generator 10 then checks the tissue impedance and delivers electrosurgical energy of predefined operating mode and power level to the loop 24 based on pressure feedback and measured impedance. Impedance measurement may be carried out by supplying a measuring current to the polyp 46 to determine is impedance as is known in the art.

Once the energy is supplied to the polyp 46 and it is severed, the position sensor 50 reports to the generator 10 of this occurrence and the generator 10 responds to the position feedback by changing operating modes (e.g., switch to coagulation mode). The mode and power settings can be changed during the procedure as a response to measured tissue impedance and loop diameter. Once the resection of the polyp 46 is complete, the energy is turned off to reduce the possibility of affecting surrounding tissue. During various stages of the procedure one or more audio and/or visual indicator may be used to signal to the surgeon that a particular stage of the procedure is completed. The audio and/or visual indicators can be disposed on the generator 10 or snare instrument 70.

Figure 6:
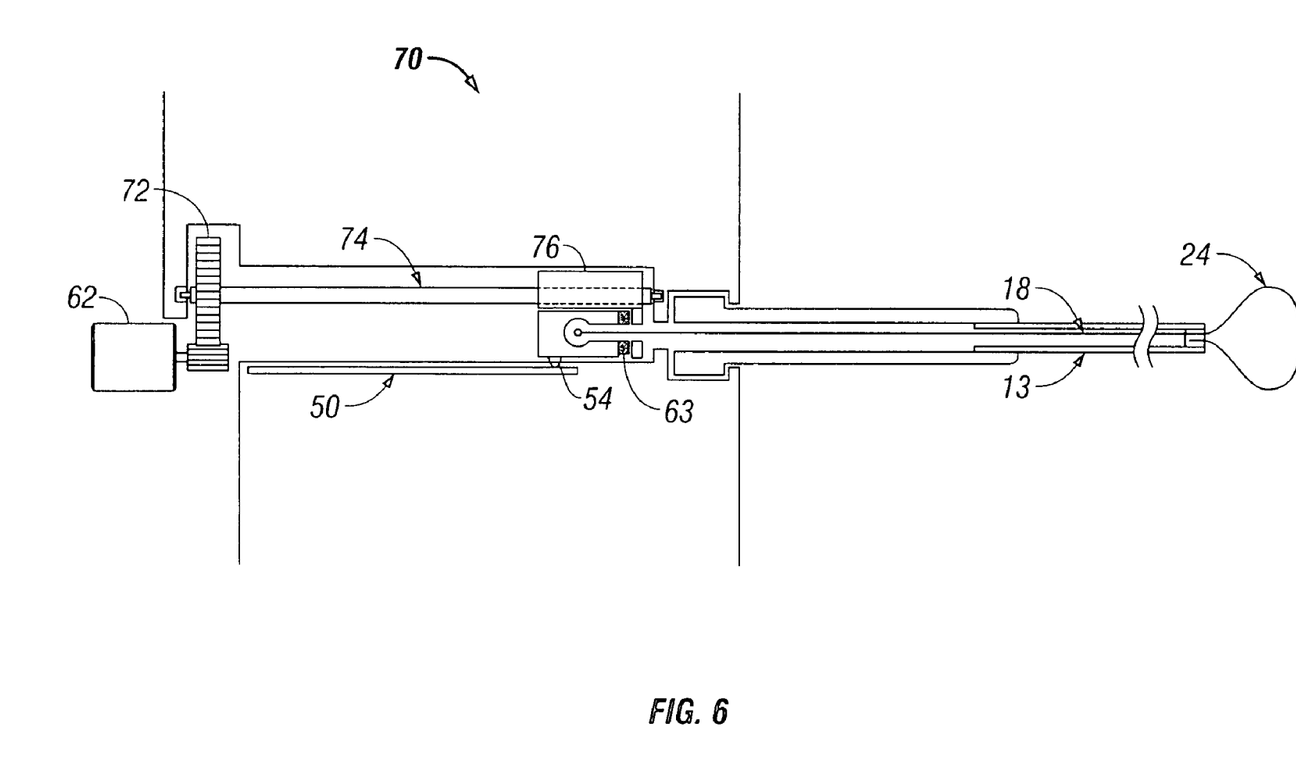
FIG. 6 is a diagram illustrating another alternate embodiment of an electrosurgical system according to the present disclosure.

FIG. 6 shows another embodiment of the snare instrument 70 that is automatically activated and monitored by the generator 10. The snare instrument 70 includes a drive motor 62 that is controlled by the generator 10. The drive motor 62 actuates a gear mechanism 72 that rotates a lead screw 74, which in turn is connected to a block 76 that includes the shaft 18. The drive motor 62 may rotate the lead screw in two directions (e.g., clockwise and counterclockwise), which then moves the block 76 and the shaft 18 backwards and forwards. The block 76 includes the nub 54 that is in contact with the potentiometer 52 to measure the diameter of the loop 24. In addition, the block 76 also includes a piezoelectric crystal 63, which converts pressure applied thereto into a corresponding voltage signal. The voltage signal may then be analyzed by the processing means of the generator 10.

The generator 10 measures pressure and size of the loop 24 and includes suitable algorithms that control the drive motor 62, through which the generator 10 controls snare pressure, snare exposure (e.g., size of the loop 24), generator mode, and generator power to optimize cautery and resection procedures.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical snare instrument comprising:
   an elongate flexible tubular sheath having proximal and distal ends, the sheath having a longitudinal axis defined therethrough;
   a shaft having proximal and distal ends, the shaft extending through and axially movable relative to the sheath;
   a snare loop provided at the distal end of the shaft configured to encircle tissue, wherein the movement of the shaft relative to the tubular sheath changes the diameter of the exposed snare loop; and
   a feedback sensor operatively coupled to the elongate tubular sheath that determines at least one condition of the snare loop, the feedback sensor including:
      a position sensor configured to measure a diameter of the snare loop, the position sensor including a potentiometer; and
      a pressure sensor configured to measure pressure exerted by the snare loop on encircled tissue.

2. An electrosurgical snare instrument as in claim 1, wherein the potentiometer is disposed on an inner surface of the sheath and a nub in contact therewith disposed on the shaft.

3. An electrosurgical snare instrument as in claim 1, wherein the pressure sensor includes a piezoelectric crystal.

4. An electrosurgical snare instrument as in claim 1, wherein the feedback sensor determines when the snare loop is fully retracted and the tissue is severed.

5. A system for performing electrosurgical procedures, comprising:
   an electrosurgical instrument including:
      an elongate tubular sheath having proximal and distal ends, the sheath having a longitudinal axis defined therethrough;
      a shaft having proximal and distal ends, the shaft extending through and axially movable relative to the sheath;

a snare loop provided at the distal end of the shaft configured to encircle tissue, wherein the movement of the shaft relative to the tubular sheath changes the diameter of the exposed snare loop; and a feedback sensor operatively coupled to the elongated tubular sheath that determines at least one condition of the snare loop, the feedback sensor including:

a position sensor configured to measure a diameter of the snare loop; and a pressure sensor configured to measure pressure exerted by the snare loop on encircled tissue; and an electrosurgical generator to provide electrosurgical energy to the electrosurgical snare instrument, the generator configured to receive feedback measurements from the electrosurgical snare instrument and to adjust electrosurgical energy as a function of the measurements.

6. A system as in claim 5, wherein the pressure sensor includes a piezoelectric crystal.

7. A system as in claim 5, wherein the generator automatically controls the movement of the shaft and diameter of the snare loop.

8. A system as in claim 5, wherein the electro surgical snare instrument includes identifying means readable by the generator, the identifying means comprising instructions to configure the generator.

9. A method for performing electrosurgical snare procedures, the method comprising the steps of:

inserting an electrosurgical snare instrument into a body cavity, the snare instrument comprising:

an elongate tubular sheath having proximal and distal ends, the tubular sheath having a longitudinal axis defined therethrough;

a shaft having proximal and distal ends, the shaft extending through and axially movable relative to the tubular sheath; and a snare loop provided at the distal end of the shaft configured to encircle tissue, wherein the movement of the shaft relative to the tubular sheath changes the diameter of the exposed snare loop to encircle a portion of the tissue;

positioning the snare loop to encircle a portion of the tissue;

collecting feedback measurements through a feedback sensor operatively coupled to the elongated tubular sheath that determines at least one condition of the snare loop indicative of at least one condition of the snare loop, the at least one condition of the snare loop including a determination of when the snare loop contacts tissue;

transmitting feedback measurements to an electrosurgical generator that provides electrosurgical energy; and adjusting electro surgical energy as a function of the feedback measurements.

10. A method as in claim 9, further comprising:

adjusting the diameter of the snare loop as a function of the feedback measurements.

11. A method as in claim 9, wherein the feedback measurements are selected from the group consisting of diameter, pressure measurements and impedance.

12. A method as in claim 9, wherein the at least one condition of the snare loop includes diameter and pressure.

13. A method as in claim 9, wherein the feedback sensor includes a potentiometer disposed on an inner surface of the tubular sheath and a nub in contact therewith disposed on the shaft.

14. A method as in claim 9, further comprising the step of determining when the snare loop is hilly retracted and the tissue is severed.

15. A system for performing electro surgical procedures, comprising:

an electrosurgical instrument including:

an elongate tubular sheath having proximal and distal ends, the tubular sheath having a longitudinal axis defined therethrough;

a shaft having proximal and distal ends, the shaft extending through and axially movable relative to the tubular sheath;

a snare loop provided at the distal end of the shaft configured to encircle tissue, wherein the movement of the shaft relative to the tubular sheath changes the diameter of the exposed snare loop; and a feedback sensor operatively coupled to the elongated tubular sheath that determines at least one condition of the snare loop; and an electrosurgical generator to provide electrosurgical energy to the electrosurgical snare instrument, the generator configured to receive feedback measurements from the electrosurgical snare instrument and to adjust electrosurgical energy as a function of the measurements, wherein the generator automatically controls the movement of the shaft and diameter of the snare loop.

16. A method for performing electrosurgical snare procedures, the method comprising the steps of:

inserting an electrosurgical snare instrument into a body cavity, the snare instrument comprising:

an elongate tubular sheath having proximal and distal ends, the tubular sheath having a longitudinal axis defined therethrough;

a shaft having proximal and distal ends, the shaft extending through and axially movable relative to the tubular sheath; and a snare loop provided at the distal end of the shaft configured to encircle tissue, wherein the movement of the shaft relative to the tubular sheath changes the diameter of the exposed snare loop to encircle a portion of the tissue;

positioning the snare loop to encircle a portion of the tissue;

collecting feedback measurements through a feedback sensor operatively coupled to the elongated tubular sheath that determines at least one condition of the snare loop indicative of at least one condition of the snare loop, the feedback measurements are selected from the group consisting of diameter, pressure measurements and impedance;

transmitting feedback measurements to an electrosurgical generator that provides electrosurgical energy; and adjusting electrosurgical energy as a function of the feedback measurements.

17. A method for performing electrosurgical snare procedures, the method comprising the steps of:

inserting an electrosurgical snare instrument into a body cavity, the snare instrument comprising:

an elongate tubular sheath having proximal and distal ends, the tubular sheath having a longitudinal axis defined therethrough;

a shaft having proximal and distal ends, the shaft extending through and axially movable relative to the tubular sheath;

a position sensor including a potentiometer disposed on an inner surface of the sheath and having a nub therewith disposed on the shaft; and a snare loop provided at the distal end of the shaft configured to encircle tissue, wherein the movement of the shaft relative to the tubular sheath changes the diameter of the exposed snare loop to encircle a portion of the tissue; positioning the snare loop to encircle a portion of the tissue; and collecting feedback measurements through a feedback sensor operatively coupled to the elongated tubular sheath that determines at least one condition of file snare loop indicative of at least one condition of the snare loop.

18. A method for performing electrosurgical snare procedures, the method comprising the steps of:

inserting an electrosurgical snare instrument into a body cavity, the snare instrument comprising:

an elongate tubular sheath having proximal and distal ends, the tubular sheath having a longitudinal axis defined therethrough;

a shaft having proximal and distal ends, the shaft extending through and axially movable relative to the tubular sheath; and a snare loop provided at the distal end of the shaft configured to encircle tissue, wherein the movement of the shaft relative to the tubular sheath changes the diameter of the exposed snare loop to encircle a portion of the tissue;

positioning the snare loop to encircle a portion of the tissue;

collecting feedback measurements through a feedback sensor operatively coupled to the elongated tubular sheath that determines at least one condition of the snare loop indicative of at least one condition of the snare loop; and determining when the snare loop is fully retracted and the tissue is severed.

* * * * *